United States Patent
Wood et al.

(10) Patent No.: US 10,925,777 B2
(45) Date of Patent: Feb. 23, 2021

(54) DIAPER ACCESSORIES AND RELATED METHODS

(71) Applicant: 3M INNOVATIVE PROPERTIES COMPANY, St. Paul, MN (US)

(72) Inventors: Leigh E. Wood, Woodbury, MN (US); Michael J. McNamara, St. Paul, MN (US); Lori-Ann S. Prioleau, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 518 days.

(21) Appl. No.: 15/535,084

(22) PCT Filed: Dec. 14, 2015

(86) PCT No.: PCT/US2015/065431
§ 371 (c)(1),
(2) Date: Jun. 12, 2017

(87) PCT Pub. No.: WO2016/100149
PCT Pub. Date: Jun. 23, 2016

(65) Prior Publication Data
US 2017/0360625 A1 Dec. 21, 2017

Related U.S. Application Data

(60) Provisional application No. 62/093,525, filed on Dec. 18, 2014.

(51) Int. Cl.
*A61F 13/15* (2006.01)
*A61F 13/494* (2006.01)
(Continued)

(52) U.S. Cl.
CPC .... *A61F 13/49406* (2013.01); *A61F 13/4946* (2013.01); *A61F 13/49058* (2013.01);
(Continued)

(58) Field of Classification Search
CPC .......... A61F 13/49406; A61F 13/49058; A61F 13/4946; A61F 13/505; A61F 13/55105; A61F 13/622; A61F 13/84
(Continued)

(56) References Cited

U.S. PATENT DOCUMENTS 4,022,210 A   5/1977   Glassman
4,968,312 A   11/1990  Khan
(Continued)

FOREIGN PATENT DOCUMENTS

EP   1 059 072 A2   12/2000
EP   1 205 169 A1   5/2002
(Continued)

OTHER PUBLICATIONS

International Search Report for PCT/US2015/065431, dated Jun. 1, 2016.

*Primary Examiner* — Jacqueline F Stephens
(74) *Attorney, Agent, or Firm* — Philip P. Soo (57) ABSTRACT

Diaper assemblies, along with related articles and methods, are provided. The diaper assembly includes a diaper comprising an inner surface and a blocking member coupled to a portion of the inner surface. The blocking member has a resilient pad coextends along a portion of the inner surface and further includes an attachment layer bonded to the resilient pad and may be repositionably attached at other locations along the inner surface. Advantageously, the blocking member can provide a releasable and repositionable seal that conveniently enhances the functionality of commercially available diapers.

14 Claims, 4 Drawing Sheets

(51) Int. Cl.
    *A61F 13/49*     (2006.01)
    *A61F 13/505*     (2006.01)
    *A61F 13/551*     (2006.01)
    *A61F 13/84*     (2006.01)
    *A61F 13/62*     (2006.01)

(52) U.S. Cl.
    CPC ...... *A61F 13/505* (2013.01); *A61F 13/55105* (2013.01); *A61F 13/622* (2013.01); *A61F 13/84* (2013.01)

(58) Field of Classification Search
    USPC ............ 604/385.11, 385.13, 385.14, 385.19
    See application file for complete search history.

(56) References Cited

U.S. PATENT DOCUMENTS

| | | | |
|---|---|---|---|
| 5,558,660 | A | 9/1996 | Dreier |
| 5,601,545 | A | 2/1997 | Glaug |
| 5,649,920 | A | 7/1997 | Lavon |
| 5,833,677 | A | 11/1998 | Sauer |
| 5,868,725 | A | 2/1999 | Coles |
| 6,258,076 | B1 | 7/2001 | Glaug |
| 6,280,426 | B1 | 8/2001 | Turner |
| 7,316,674 | B2 | 1/2008 | Infantino |
| 7,842,020 | B2 | 11/2010 | Hurwitz |
| 7,842,021 | B2 | 11/2010 | Wood |
| 2002/0143316 | A1* | 10/2002 | Sherrod ................ A61F 13/505 604/385.101 |
| 2003/0050616 | A1 | 3/2003 | Reynolds |
| 2004/0147889 | A1* | 7/2004 | Roe ................... A61F 13/15203 604/369 |
| 2006/0058767 | A1 | 3/2006 | Zhang |
| 2006/0058768 | A1 | 3/2006 | Zhang |
| 2012/0059344 | A1 | 3/2012 | Seo |
| 2012/0204383 | A1 | 8/2012 | Wood |
| 2014/0257229 | A1* | 9/2014 | Wang ................. A61F 13/4906 604/385.14 |

FOREIGN PATENT DOCUMENTS

| | | |
|---|---|---|
| EP | 2 042 140 | 4/2009 |
| EP | 2 042 141 A1 | 4/2009 |
| JP | 2003-299689 | 10/2003 |
| JP | 2009-034270 | 2/2009 |
| WO | WO 96/29037 | 9/1996 |
| WO | WO 97/22321 | 6/1997 |

\* cited by examiner

DIAPER ACCESSORIES AND RELATED METHODS

CROSS REFERENCE TO RELATED APPLICATIONS

This application is a national stage filing under 35 U.S.C. 371 of PCT/US2015/065431, filed Dec. 14, 2015, which claims the benefit of U.S. Provisional Patent Application No. 62/093,525, filed Dec. 18, 2014, the disclosures of which are incorporated by reference in their entirety herein.

FIELD OF THE INVENTION

Provided herein are assemblies and methods relating to accessories for absorbent articles. More particularly, the absorbent articles are wearable absorbent articles.

BACKGROUND

Diapers are a type of underwear that allow for discrete defecation or urination without use of a toilet. Commonly, diapers are worn by infants, but they may also be configured for use by adults coping with incontinence issues. Those who use diapers may wear them at any time of day or night and for extended periods of time. For the sake of convenience, diapers are optionally disposable and are engineered according to the size of the wearer, the wearer's gender, the particular use of the diaper contemplated, and other considerations such as skin sensitivities or other user preferences.

Those wearing diapers are generally unable to control their excretion, so fluids and other matter may be deposited into the diaper at any time. When this occurs, it is desirable to retain the fluids and other matter within the diaper to prevent leakage. Containing the bodily waste of an infant in a diaper can be technically challenging, and especially so when the infant is breast-fed, which often results in watery feces. The problem of containment can be compounded by illness, which can result in messy bowel movements. An infant may also have a bowel movement in an abrupt and unexpected manner, commonly referred to as a "blow out," making effective leak prevention very difficult.

SUMMARY

Prior attempts to solve the aforementioned problems have focused on providing enhanced diapers with an improved seal around the waistline of the wearer. Such enhancements have included, for example, a folded, stacked, or pleated waist seal or other leak-proof guard that fits snugly around the waistline of the infant when the diaper is worn. While these solutions may be effective, they lack versatility. The incorporated seals add significant bulk to the diaper and are present whether or not they are needed. With disposable diapers, these seals are discarded along with the rest of diaper, resulting in waste. Further, they cannot be moved or adjusted to adapt to the specific contours of the wearer's body. Finally, these diapers do not offer ease of use over a wide range of existing diaper configurations. The provided diaper accessories address all of these shortcomings.

In a first aspect, a diaper assembly is provided. The diaper assembly comprises: a diaper comprising an inner surface; and a blocking member coupled to a portion of the inner surface, the blocking member comprising: a resilient pad coextensive with the portion of the inner surface; and an attachment layer bonded to the resilient pad and capable of being repositionably attached to the inner surface at a plurality of locations.

In a second aspect, a method of reducing leakage from a diaper is provided, the method comprising the steps of: providing a blocking member having a resilient pad and an attachment layer bonded to the resilient pad, the attachment layer being attachable to an inner surface of the diaper; coupling the attachment layer to a portion of the inner surface to provide a diaper assembly, wherein the blocking member is coextensive with the portion of the inner surface; and fastening the diaper assembly to a wearer whereby the blocking member conforms to contours of the wearer's back and prevents any discharged bodily waste from leaking out of the diaper.

In a third aspect, a packaged assembly is provided, comprising: a container; and a plurality of blocking members received in the container, each blocking member comprising a resilient pad and an attachment layer bonded to the resilient pad, the attachment layer having a configuration allowing releasable attachment to an inner surface of a diaper.

BRIEF DESCRIPTION OF THE DRAWINGS

Exemplary embodiments shall be further described with reference to the following drawings.

DEFINITIONS

As used herein:

"diaper" refers to an absorbent article that is generally worn by infants or incontinent persons that is worn around the lower torso of the wearer;

"disposable" means articles that are not intended to be laundered or otherwise restored or reused after use; and "resiliently compressible" material refers to a material that compresses to at least 50 percent of its uncompressed thickness under a load of 250 grams per square centimeter and recovers to at least 80 percent of its original thickness after being compressed to 50 percent of its original thickness for 10 minutes, wherein recovery occurs within 30 seconds after removal of compressive force.

DETAILED DESCRIPTION

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

Figure 1:
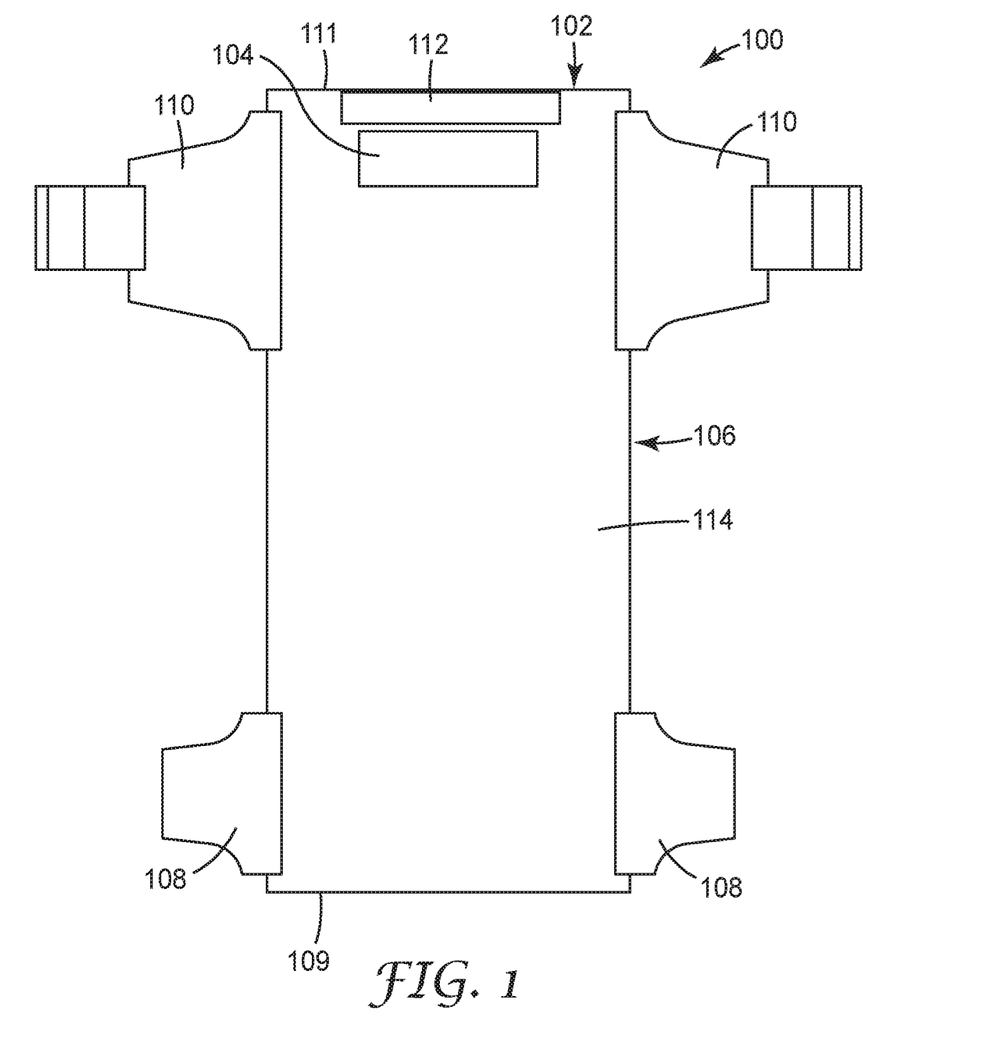
FIG. 1 is a plan view of an exemplary finished diaper assembly.

A diaper assembly according to one exemplary embodiment is depicted in FIG. 1 and hereinafter referred to by the numeral 100. The diaper assembly 100 is shown in its flattened state. Portions of the diaper assembly 100 intended to face or contact the wearer are oriented toward the viewer in FIG. 1.

As shown, the diaper assembly 100 generally includes a diaper 102 and a blocking member 104 coupled to the diaper 102. The diaper 102, in turn, is comprised of a generally rectangular-shaped body 106 having a front edge 109 and a rear edge 111, a pair of opposing front ears 108 coupled to lateral sides of the body 106 adjacent the front edge 109, and a pair of opposing rear ears 110 coupled to lateral sides of the body 106 adjacent the rear edge 111. As an optional component, the diaper 102 further includes a rear elastic waistband 112 aligned along the rear edge 111 of the body 102. In this embodiment, the blocking member 104 has an elongated shape oriented approximately parallel to that of the waistband 112, or more generally, the rear edge 111 of the diaper 102.

It is understood that many variants are possible. For example, the blocking member 104 can partially or fully overlap with the waistband 112. The waistband 112, which can have any reasonable length and width, may have a shape that is quite different from that shown in FIG. 1.

The body 106 has an inner surface 114 that is absorbent. Although not intended to be limiting here, the inner surface 114 may comprise a water-permeable top sheet that extends over additional components of the body 106 that are not visible here. For example, the permeable top sheet may extend over an absorbent member, which in turn extends over a liquid impermeable backing. Further options and advantageous features related to the diaper 102 are described in U.S. Pat. No. 7,842,021 (Wood et al.).

When worn, the diaper assembly 100 assumes a "U" shape, with the front and rear edges of the body 106 collectively encircling the waist of the wearer.

The blocking member 104 is releasably attachable to the inner surface 114 of the body 106 and, when the diaper 102 is worn, forms a seal between the inner surface 114 and intergluteal cleft, slightly below the small of the back, of the wearer. In the event of a sudden bowel movement, this seal prevents bodily waste from being discharged outwards and reaching the rear edge 111 of the body 106. The seal can also help prevent such waste from reaching the rear edge 111 as a result of subsequent pressure on the diaper and bodily movement of the wearer.

The blocking member 104 is generally placed on the diaper 102 before the diaper 102 is worn, although in certain pants-style diapers it may be preferable to place the blocking member in the diaper after the diaper is pulled up. Preferably, the blocking member 104 is repositionable, so that the location and orientation of the blocking member 104 along the inner surface 114 can be manually adjusted after initial placement of the blocking member 104 on the body 106. In such cases, the blocking member 104 may be detached and re-attached at a plurality of different locations closer to or further away from the rear edge 111 to improve the seal against the wearer.

Figure 2:
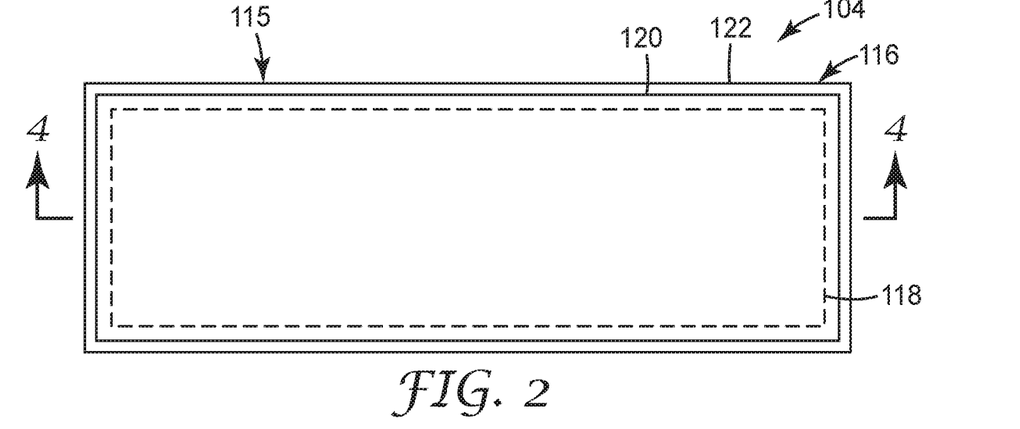
FIG. 2 is a plan view of a diaper accessory used in the finished diaper of FIG. 1 according to an exemplary embodiment, showing its top surface.
Figure 3:
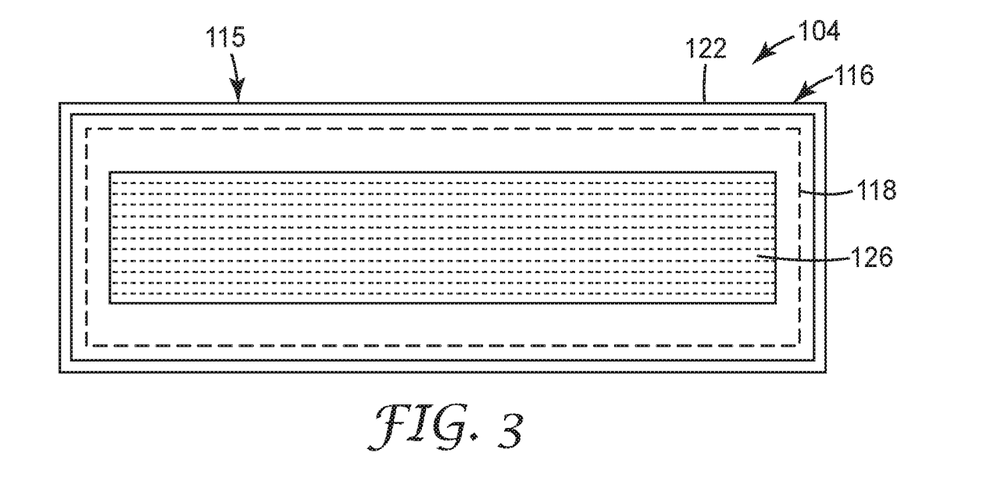
FIG. 3 is a plan view of the diaper accessory of FIG. 2, showing its bottom surface.
Figure 4:
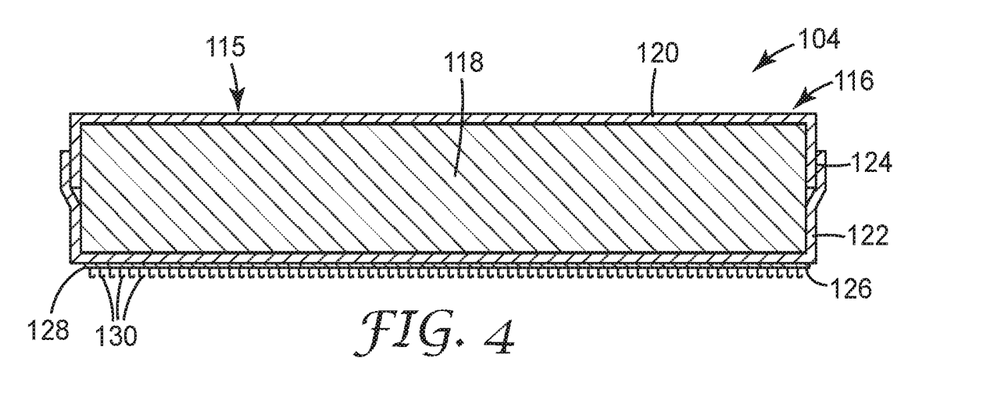
FIG. 4 is a side cross-sectional view of the diaper accessory of FIGS. 1-2, representing plane 4-4 in FIG. 1.

The blocking member 104 of the diaper assembly 100 is shown in more detail in FIGS. 2-4. Referring first to FIG. 2, showing a view of its top-facing surfaces, the blocking member 104 includes a resilient pad 115 comprised of a shell 116 surrounding an embedded core member 118. In FIGS. 2 and 3, the core member 118 is normally hidden but shown in dotted lines for illustrative purposes.

Optionally and as shown, the shell 116 is a two-part component having a top shell layer 120 and a bottom shell layer 122. As shown in the cross-sectional view of FIG. 4, the peripheral edges of the top shell layer 120 are permanently sealed with the peripheral edges of the bottom shell layer 122 along a seam 124 to provide an enclosure that snugly fits the core member 118. The seam 124 may extend fully around the perimeter of the core member 118 or just a portion thereof, provided that the core member 118 is adequately secured. The seam 124 between the top and bottom shell layers 120, 122 may be sealed using any of a number of methods known in the art, including for example lamination, adhesive bonding, ultrasonic bonding, compression bonding, surface bonding, stitching, taping, and combinations thereof.

While the shell 116 and core member 118 are shown in direct contact with each other for simplicity, it is understood that one or more additional layers could be interposed between them for functional and/or decorative purposes, and either component itself could include two or more layers, if desired. For example, the core member 118 could be partially or fully surrounded by an adhesive layer that bonds the core member 118 to the shell 116 to reduce, or eliminate, unwanted sliding of these components relative to each other.

Being intended for contact with the wearer's skin, the shell 116 is preferably made from a material that is soft to the touch. In some embodiments, the shell 116 is made from a non-woven material. Preferred nonwoven materials include polyolefin nonwoven materials. The type of nonwoven material is not restricted and may include, for example, bonded carded nonwoven web, spunbond nonwoven web, spunlaced nonwoven web, meltblown nonwoven web, airlaid nonwoven web, and combinations thereof.

The core member 118 can be made from any of a number of different resiliently compressible materials. Especially suitable materials include closed-celled polyethylene foams, open-celled polyurethane foams, and high-loft batting materials. Broadly speaking, however, possible materials can include gauze, cloth, paper, sponge, plastic, or any other material capable of improving leak prevention that does not adversely affect the wearer's comfort and/or health.

Foam materials are beneficial because of their ability to significantly compress, providing greater comfort to the wearer of the diaper assembly 100. In preferred embodiments, the foam is resiliently compressible.

Suitable batting materials include batting materials made from cotton, polyester, and/or wool. These materials are also preferably resiliently compressible.

In some embodiments, the resilient pad 115 has an overall thickness that is sufficiently thick to provide an adequate seal but also thin enough to be comfortable for the wearer. The thickness, which is defined here as along directions perpendicular to the inner surface, preferably ranges from 5 millimeters to 20 millimeters. Thicknesses outside of this range, however, may be appropriate depending on the stiffness and compressibility of the resilient pad 115.

Besides the thickness, other dimensions of the resilient pad 115 can also affect the performance of the blocking member 104. To safeguard against leakage around the blocking member 104, the resilient pad 115 preferably has an elongated shape, such as that of a rectangular prism as shown in the drawings. While the length is not critical, certain embodiments of the resilient pad 115 have a length dimension that extends along the rear edge 111 of the diaper. This length, if defined along a direction parallel to the rear edge 111, could range for example between 35 millimeters and 150 millimeters as measured when the resilient pad is in its relaxed (uncompressed) configuration.

The shape of the blocking member 104 is not especially limited. In certain embodiments, the blocking member 104 may be in the shape of a band, a line, a dot, a square, a rectangle, a circle, an arc, a diamond, a trapezoid, or any other shape that can be disposed in the diaper such that the leak resistance of the diaper is improved.

The front-to-back dimension of the resilient pad 115 should be sufficient to prevent solid and liquid waste from traversing the blocking member 104 when the diaper assembly is worn over a reasonable period of time. In some embodiments, the resilient pad has a front-to-back width ranging between 10 millimeters and 50 millimeters when relaxed.

Optionally, the core member 118 is at least somewhat absorbent, enabling the blocking member 104 to not only block passage of liquid and solid waste but also act to retain within it some of this waste matter. Such a feature might provide enhanced comfort to the wearer, for example, if the diaper were to become saturated. Materials useful for this purpose include super absorbent gels, such as polyacrylate absorbents, and open-celled hydrophilic foams.

As shown in FIGS. 3 and 4, the blocking member 104 further includes an attachment layer 126 that extends over and contacts the outer-facing surface of the bottom shell layer 122. The attachment layer 126 may be fastened to the bottom shell layer 122 using a pressure sensitive adhesive, hot melt adhesive, ultrasonic bonding, compression bonding, surface bonding, or using a mechanical fastening mechanism. Further, the size of the attachment layer 126 is not critical and can be adjusted to be larger or small in area to balance the need to secure the blocking member 104 during use against ease of removability in case adjustment or reuse is desired.

In some embodiments, the attachment layer 126 has a configuration that enables releasable coupling to the inner surface of a commercially available diaper, such as shown in FIG. 1. Many such configurations are possible. In some embodiments, the attachment layer 126 employs the male member of a mechanical fastener attached to its outer surface. This is the case in FIG. 4, which shows a hook portion of a loop and hook attachment system. In the figure, the attachment layer 126 has a base layer 128 and a plurality of tiny, replicated hooks 130 disposed according to a two-dimensional pattern that are integral with the base layer 128 and protrude outwardly in a direction normal to the base layer 128 away from the blocking member 104. This advantageously allows repositionable attachment of the blocking member 104 to a nonwoven top sheet of many commercially available diapers, without damage to either the blocking member 104 or the diaper.

One exemplary attachment system uses a mechanical fastening strip that includes a backing with upstanding hooks or posts with loop engaging overhangs that are capable of mechanically engaging a fibrous target area. The fibrous target area is typically made from a nonwoven material, although woven materials could also be used. Preferably, the target area extends over a large surface area along the inner surface of the diaper to enable the blocking member 104 to be reoriented and repositioned over a wide range of locations. Optionally, the target area is essentially coextensive with the inner surface, allowing the blocking member 104 to be secured anywhere along the inner surface and easily detached, if desired, by peeling the blocking member 104 away from the inner surface of the diaper. In an exemplary embodiment, the above backing is slit to form a two-dimensional pattern and subsequently stretched along transverse directions to form a reticulated fastening strip, as described in U.S. Patent Publication No. 2012/0204383 (Wood et al.).

In some embodiments, combinations of two or more attachment mechanisms may be used. For example, the attachment layer 126 may include both a two-dimensional array of hooks and an adhesive. These attachment mechanisms may be disposed over the same areas or different areas of the bottom shell layer 122. If a reticulated fastening strip is used, an adhesive layer could be disposed in the interstitial areas.

To save material costs, the attachment layer 126 can be made discontinuous. In one embodiment, the attachment layer 126 is comprised of a pair of fastening strips that are parallel and spaced apart from each other, where each fastening strip extends along the length of the blocking member 104 adjacent a respective peripheral edge of the bottom shell layer 122.

These embodiments are not exhaustive and the attachment layer 126 can assume many other configurations that serve the functions described above, including layers that increase the coefficient of friction between the resilient pad 115 and the diaper and prevent relative movement.

Methods of making the blocking member 104 are not particularly restricted. While the blocking member 104 can be manually assembled, its layered construction makes it especially suitable for a continuous manufacturing process. One method of making one embodiment of the blocking member of the present invention is illustrated in FIG. 5.

Figure 5:
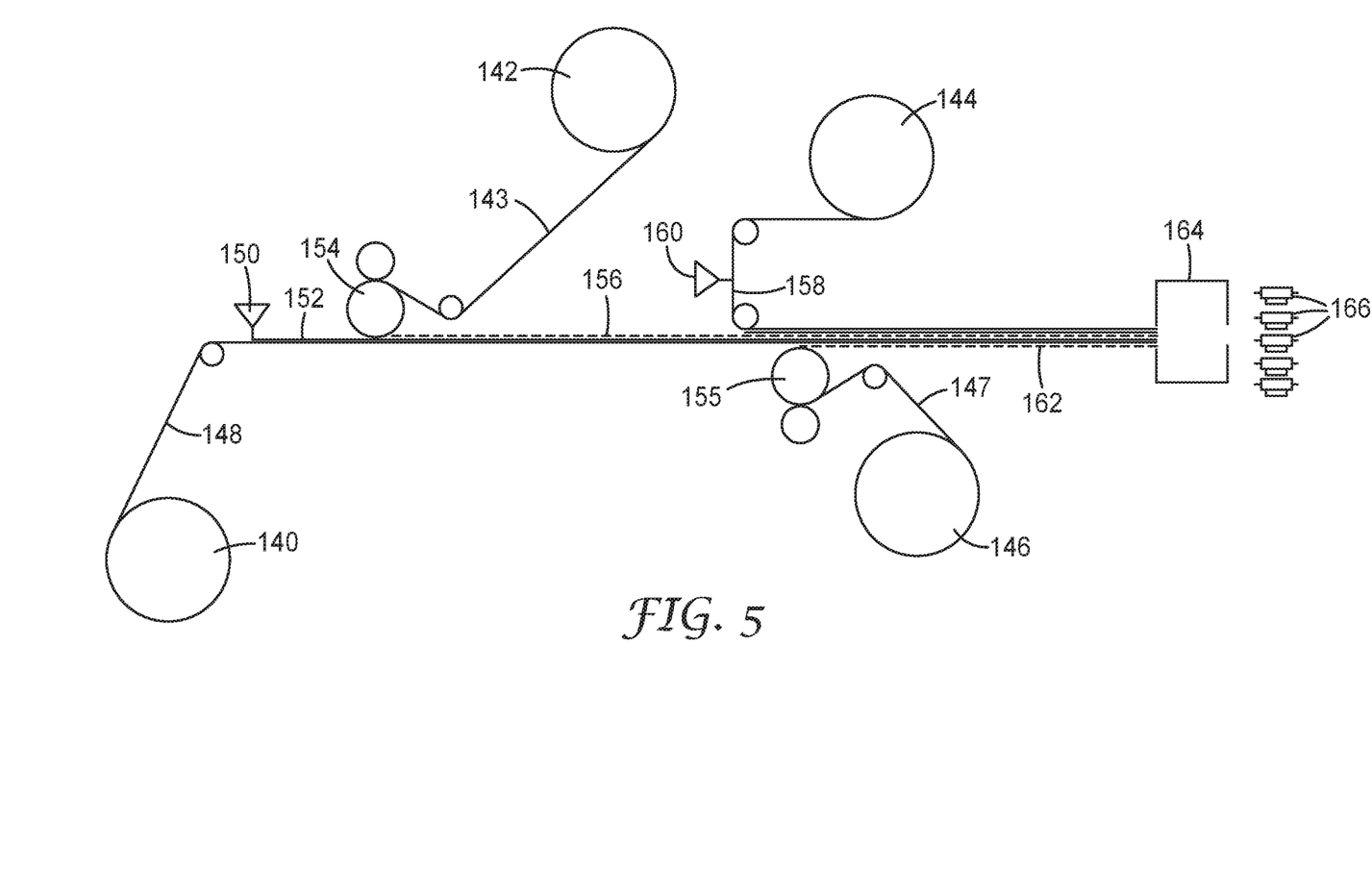
FIG. 5 is a schematic showing an exemplary continuous method of manufacturing the diaper accessories of FIGS. 2-4.

Referring now to FIG. 5, the continuous process uses four feed rolls: a first nonwoven roll 140, a core roll 142, a second nonwoven roll 144, and an attachment layer roll 146. Starting with the first nonwoven roll 140, a nonwoven web 148 is unwound and directed using a guide roll to an adhesive applicator 150, which deposits a thin layer of adhesive 152 on its top surface. The web 148 is then conveyed to a cutting and placement apparatus 154 which guides a continuous core layer 143 from the core roll 142, cuts the continuous layer into discrete pieces 156, and places the discrete pieces 156 in a spaced relationship onto the adhesive surface of the web 148. A similar process to the above then disposes onto the exposed surface of the discrete pieces of core layer 156 an adhesive-coated non-woven layer 158 from the nonwoven roll 144 and adhesive applicator 160. Finally, a continuous attachment layer 147 is unwound from the attachment layer roll 146. The continuous attachment layer 147 is conveyed to a second cutting and placement apparatus 155 which guides the continuous attachment layer 147 from the attachment layer roll 146, cuts the continuous attachment layer into discrete pieces 162, and places the discrete pieces 162 onto the bottom surface of the web 148.

Referring for a moment back to FIG. 4, if the attachment layer is a mechanical fastener having replicated hooks 130, it may be coated with a pressure sensitive adhesive on the base layer 128 opposite the hooks 130. Alternatively, the attachment layer may be coated with an adhesive in-line with a third adhesive applicator (not shown) positioned before the second cutting and placement apparatus 155.

In other embodiments, the attachment layer may be bonded directly to the core pieces 156, with no nonwoven layers present. In yet other embodiments the attachment layer 147 may be an adhesive instead of a mechanical fastener, and the adhesive may be supplied as a transfer tape or may be coated directly onto the blocking member. In this embodiment, the adhesive can be covered by a release liner to protect the exposed adhesive. In still other embodiments, bonding may be achieved by ultrasonic bonding or bonding with heat and pressure, and the adhesive applicators may be replaced with other bonding stations.

With all layers thus mutually bonded, the web 148 is conveyed to a converting station 164 that cuts the continuous web 148 (and its adjoining layers) into a plurality of discrete blocking members 166. In some embodiments, this cutting process is carried out by die cutting (such as rotary die cutting), cross-slicing using a cutting blade, or even laser conversion. Thus made, the blocking members 166 can then be individually wrapped or otherwise packaged as appropriate for the desired end user application.

Figure 6:
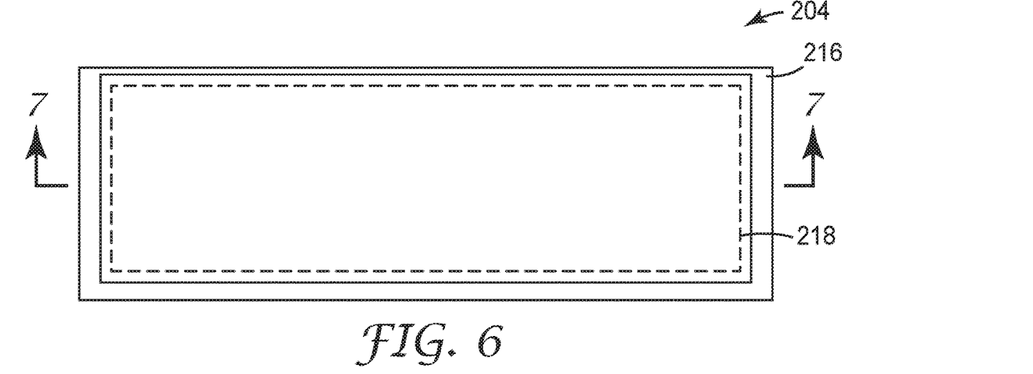
FIG. 6 is a plan view of a diaper accessory according to another exemplary embodiment, showing its top surface.
Figure 7:
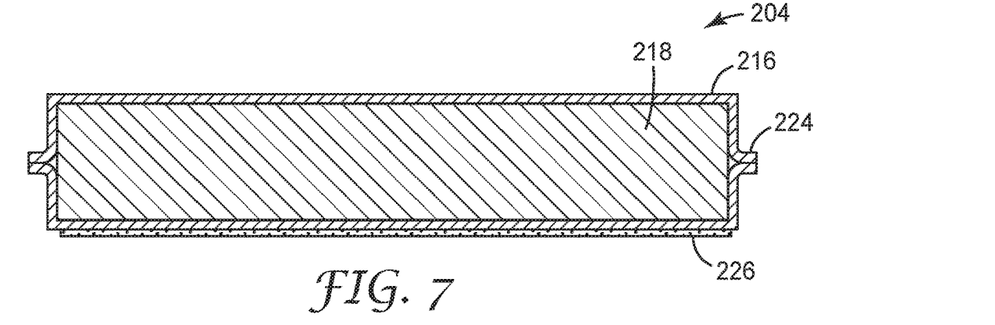
FIG. 7 is a side cross-sectional view of the diaper accessory, representing plane 7-7 in FIG. 6.

FIGS. 6-7 show an alternative configuration for a blocking member 204 that may be used with the diaper 102 in FIG. 1. The blocking member 204 is akin to the blocking member 104 in many respects, including its size, shape and function, but uses a one-piece shell 216 that is folded down the middle to provide a "clam shell" pocket that accommodates a core member 218. Three sides of the shell 216, as folded, are then sealed to form a seam 224 as shown in FIG. 7, extending along a rectangular pocket. The seam 224 may be secured by thermal bonding or any other method previously described with respect to the seam 124. The core member 218 can then be inserted into the pocket and the fourth side of the shell 216 sealed.

Another difference between the blocking member 204 and the prior embodiment is the use of an adhesive layer 226 for attachment to the inner surface of a diaper. The adhesive layer 226 is preferably composed of a pressure sensitive adhesive (PSA) that exhibits tack at room temperature (e.g., about 20° C. to about 25° C.), as can be determined by a finger tack test or by conventional measurement devices. The pressure sensitive adhesive can easily form a useful adhesive bond with the application of light pressure, while enabling subsequent release from the inner surface of a diaper with only a moderate peeling force. Preferably, no adhesive residue or damage is evident even upon repeated repositioning of the blocking member 204 along the inner surface of a diaper.

In some embodiments, the adhesive layer 226 is compressible, enabling it to conform to rough or uneven surfaces and achieve good adhesion. In some embodiments, the adhesive layer 226 is a dual-sided foam tape that is resiliently compressible. In any case, it is preferred that the adhesive layer 226 is permanently bonded to the core member 218, yet capable of being releasably bonded to the inner surface of a diaper.

To provide optimal releasability and repositionability of the blocking member 204, the PSA layer may be discontinuous. The term "discontinuous" as used herein means that the PSA layer comprises voids such that the layer adjacent to the PSA layer (e.g. the shell 216) is not entirely covered by the PSA layer. In some embodiments, the PSA layer may take the form of islands of PSA disposed upon a heat-bondable carrier film or, alternatively, coated directly onto the shell 216.

Such islands of PSA may have a specific shape (e.g. dots, stripes, or triangles) or irregular shapes. In some embodiments, the sheet of PSA may be microperforated or microstructured. In still further embodiments, the discontinuous PSA layer may be in the form of a web of pressure sensitive adhesive fibers defining voids through which the bottom surface of the shell 216 is exposed.

Further aspects of the blocking member 204 are essentially analogous to those already described with respect to the blocking member 104 and therefore will not be repeated here.

Figure 8:
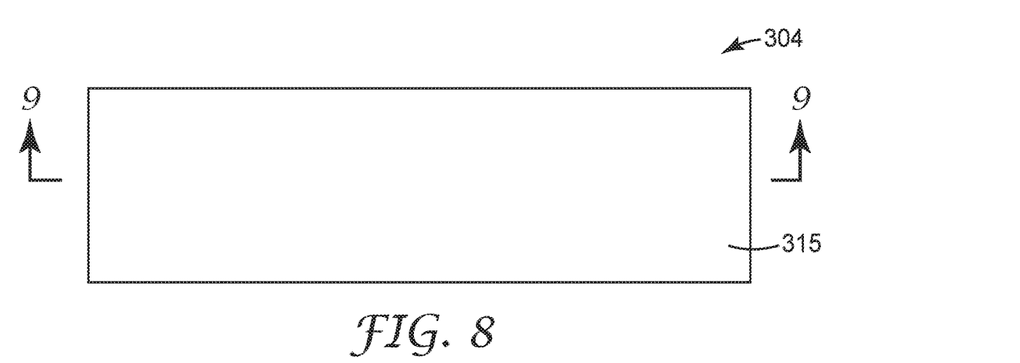
FIG. 8 is a plan view of a diaper accessory according to still another exemplary embodiment.
Figure 9:
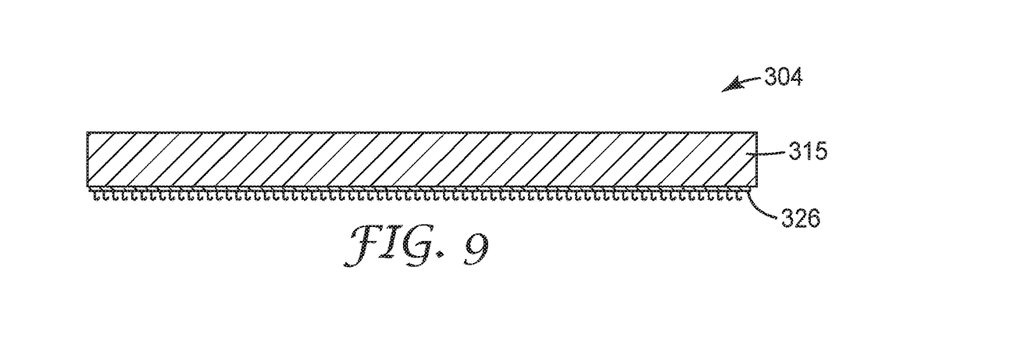
FIG. 9 is a side cross-sectional view of the diaper accessory, representing plane 9-9 shown in FIG. 8.

FIGS. 8 and 9 show a blocking member 304 according to still another embodiment, in which the shell and core member have been merged into a resilient pad 315 that is monolithic. An attachment layer 326 is affixed to the bottom side of the resilient pad 315, enabling it to releasably couple to the inner surface of a diaper. Although the attachment layer 326 uses a two-dimensional pattern of hooks like that of attachment layer 126 in FIGS. 2-4, it is to be understood that it could use any releasable coupling mechanism known to one skilled in the art. While not shown here, the attachment layer 326 could optionally be integrated into the resilient pad 315.

It is noted that the blocking member 204 could be made using a continuous manufacturing route similar to that described above and illustrated in FIG. 5, with any necessary adaptations.

The diaper accessories described here may optionally be packaged as an assembly that enables them to be conveniently stored and dispensed by a caregiver. One exemplary packaged assembly uses a container, such as a box or cylindrical canister. The container optionally has a lid that releasably encloses an open end. Received in the container is a plurality of blocking members that are easily accessed by a caregiver when placing or changing a diaper. Optionally, the plurality of blocking members are stacked for easy access from the open end of the container. In an alternative embodiment, the plurality of blocking members are interconnected by a thin, frangible webbing and wound in a spooled configuration. A caregiver can unwind the roll to dispense the blocking members through the open end, tearing off one blocking member at a time as needed.

The above diaper assemblies and accessories can be advantageously used in any of a number of ways. When it is suspected that the wearer may need added leakage protection, the blocking member can be releasably attached to the diaper by positioning and then pressing down on the attachment layer against a portion of the inner surface of the diaper. Preferably, the blocking member is coextensive with the portion of the inner surface such that the blocking member would not visibly protrude beyond the edges of the diaper when the diaper assembly is worn. The diaper assembly can be easily fastened to the wearer using diaper tabs according to the instructions of the diaper manufacturer.

As previously mentioned, the blocking member can be repositioned to accommodate the shape of the wearer's body. In the event that the diaper assembly is not soiled, the blocking member can be subsequently detached for re-use with a different diaper. Advantageously, the blocking member can be used "on demand," such that it is only implemented when the caregiver anticipates a need for extra protection, such as when the wearer is ill or, for any other reason, particularly likely to have a runny or messy bowel movement.

Additional embodiments, not intended to be exhaustive, are enumerated below:

1. A diaper assembly comprising: a diaper comprising an inner surface; and a blocking member coupled to a portion of the inner surface, the blocking member comprising: a resilient pad coextensive with the portion of the inner surface; and an attachment layer bonded to the resilient pad and capable of being repositionably attached to the inner surface at a plurality of locations.

2. The diaper assembly of embodiment 1, wherein the diaper further comprises: a top sheet that is permeable to water; a backing that is impermeable to water; and an absorbent member disposed between the top sheet and the backing.

3. The diaper assembly of embodiment 1 or 2, wherein the resilient pad comprises an absorbent material.

4. The diaper assembly of embodiment 1 or 2, wherein the resilient pad comprises a resilient core and a shell at least partially surrounding the resilient core, wherein the attachment layer is bonded to the shell.

5. The diaper assembly of embodiment 4, wherein the shell comprises a nonwoven web.

6. The diaper assembly of embodiment 5, wherein the nonwoven web has a basis weight ranging between 5 gsm and 50 gsm.

7. The diaper assembly of embodiment 5, wherein the nonwoven web comprises a polyolefin.

8. The diaper assembly of embodiment 5, wherein the nonwoven web is selected from the group consisting of: a bonded carded nonwoven web, spunbond nonwoven web, spunlaced nonwoven web, meltblown nonwoven web, airlaid nonwoven web, and combinations thereof.

9. The diaper assembly of any one of embodiments 1-8, wherein the attachment layer has an outer surface and a male element of a mechanical fastener disposed on the outer surface.

10. The diaper assembly of embodiment 9, wherein the male element of the mechanical fastener comprises a replicated hook material.

11. The diaper assembly of claim 10, wherein the replicated hook material is reticulated.

12. The diaper assembly of claim 10 or 11, wherein the replicated hook material is bonded to the resilient pad according to a discontinuous pattern.

13. The diaper assembly of any one of embodiments 9-12, wherein the diaper comprises a nonwoven top sheet that engages, and mechanically retains, the male element of the mechanical fastener.

14. The diaper assembly of any one of embodiments 1-8, wherein the attachment layer comprises a pressure sensitive adhesive.

15. The diaper assembly of embodiment 12, wherein the pressure sensitive adhesive is discontinuous.

16. The diaper assembly of any one of embodiments 1-13, wherein the attachment layer is bonded to the resilient pad using a pressure sensitive adhesive, hot melt adhesive, ultrasonic bonding, compression bonding, or surface bonding.

17. The diaper assembly of any one of embodiments 1-16, wherein the resilient pad comprises a foam or polyester batting.

18. The diaper assembly of embodiment 17, wherein the foam comprises a closed-cell polyethylene foam or an open-cell polyurethane foam.

19. The diaper assembly of embodiment 17 or 18, wherein the foam compresses to at least 50 percent of its uncompressed thickness under a load of 250 grams per square centimeter and recovers to at least 80 percent of its original thickness after being compressed to 50 percent of its original thickness for 10 minutes, wherein recovery occurs within 30 seconds after removal of compressive force.

20. The diaper assembly of any one of embodiments 1-19, wherein the resilient pad has a thickness, defined along a direction perpendicular to the inner surface, ranging from 5 millimeters to 20 millimeters.

21. The diaper assembly of any one of embodiments 1-20, wherein the diaper has a rear edge and wherein the blocking member has an elongated shape aligned along the rear edge.

22. The diaper assembly of embodiment 21, wherein the resilient pad has a length, defined along a direction parallel to the rear edge, ranging between 35 millimeters and 150 millimeters.

23. The diaper assembly of any one of embodiments 1-22, wherein the resilient pad has a front-to-back width ranging between 10 millimeters and 50 millimeters when in its relaxed, uncompressed state.

24. The diaper assembly of any one of embodiments 1-23, wherein the blocking member is detachable from the inner surface by peeling the blocking member away from the inner surface.

25. A method of reducing leakage from a diaper, comprising the steps of: providing a blocking member having a resilient pad and an attachment layer bonded to the resilient pad, the attachment layer being attachable to an inner surface of the diaper; coupling the attachment layer to a portion of the inner surface to provide a diaper assembly, wherein the blocking member is coextensive with the portion of the inner surface; and fastening the diaper assembly to a wearer whereby the blocking member conforms to contours of the wearer's back and prevents any discharged bodily waste from leaking out of the diaper.

26. The method of embodiment 25, wherein the attachment layer is releasably attachable to the inner surface of the diaper.

27. The method of embodiment 25 or 26, wherein the attachment layer is repositionable such that the blocking member can be subsequently detached from the inner surface and reattached to a different portion of the inner surface of the same or a different diaper.

28. The method of any one of embodiments 25-27, wherein the attachment layer comprises a male component of a mechanical fastener and the inner surface comprises a female component of the mechanical fastener capable of engaging with the male component.

29. The method of any one of embodiments 25-27, wherein the attachment layer comprises a pressure sensitive adhesive capable of bonding to the inner surface of the diaper.

30. The method of embodiment 29, wherein the pressure sensitive adhesive is capable of being repeatably attached to the same or a different location of the inner surface without damaging either the diaper or the blocking member.

31. A packaged assembly comprising: a container; and a plurality of blocking members received in the container, each blocking member comprising a resilient pad and an attachment layer bonded to the resilient pad, the attachment layer having a configuration allowing releasable attachment to an inner surface of a diaper.

32. The packaged assembly of embodiment 31, wherein each blocking member generally has the shape of a rectangular prism.

33. The packaged assembly of embodiment 31 or 32, wherein the attachment layer has an outer surface and a male element of a mechanical fastener disposed on the outer surface.

EXAMPLES

Objects and advantages of this disclosure are further illustrated by the following non-limiting examples, but the particular materials and amounts thereof recited in these examples, as well as other conditions and details, should not be construed to unduly limit this disclosure.

Unless otherwise noted, all parts, percentages, ratios, etc. in the Examples and the rest of the specification are by weight.

Test Methods

To test for ability to effectively prevent viscous material from traveling along the hollow of the small of the back of an infant wearing a diaper with the blocking member of this invention the following procedure was used.

A 18 inch length of a hollow paper tube, with an inner diameter of 6 inches and wall thickness of 0.25 inches was prepared and fitted on the external surface with a 30 cm by 18 cm piece of 2.5 mm thick neoprene rubber placed lengthwise to cover about half of the circumference of the tube aligned with one end. This rubber piece was attached to the tube with pressure sensitive adhesive double coated tape. A second piece of neoprene rubber with the same dimensions was prepared by creating a funnel shaped opening with an X-ACTO brand knife (available from Elmer's Products, Inc. in Westerville, Ohio), wherein the small end of the funnel shape was about 2 inches in length and about 20 mm wide at the top surface and about 18 mm wide at the bottom surface, prepared by cutting the small end of the funnel shape at about a 45 degree angle to simulate the small of the back of an infant. The end of the small end of the funnel shape away from the wide end of the shape provided an opening in the funnel shaped cut out. The wide end of the funnel shape was about 3 inches wide at the widest and taped to the inner end of the small end of the funnel shape. The length of the wide end of the funnel shape, in the direction of the funnel, was about 3 inches. This cut piece of rubber was attached in face to face manner to the first piece of rubber on the tube using pressure-sensitive-adhesive double coated tape. A piece of a loop material of a hook and loop system was attached to the tube in the area between the ends of the rubber that were attached to the tube.

About a tablespoon of chocolate pudding was placed in the funnel shaped opening at the top (inside) end of the narrow end of the shape. A diaper to be tested is placed over this such that the rear waist of the diaper is adjacent the end of the tube (and the outer end of the funnel shape) and tensioned and held in place by using the hook closure tabs of the diaper to attach to the loop material on the tube. This hold the diaper under tension as it would be on an infant wearing the diaper, wherein the tension is proved by the elastic ears of the diaper being stretched. A 4.5 pound roller (rubber covered, 3 inch outer diameter) is placed on the diaper below (away from the rear waist) where the tablespoon of pudding is located between the diaper and the tube. The roller is rolled over the area of the diaper overlaying the pudding and all the way to the waist end of the diaper. At this point an observation is made as to whether or not any of the pudding was pushed out beyond the waist of the diaper. If no pudding is observed being pushed out of the end of the diaper the roller is passed two more times over the area toward the waist end. An observation of whether any pudding was pushed past the end of the diaper is made after each of these subsequent passed of the roller. At the end of the test the diaper is removed and the test apparatus cleaned by wiping away excess pudding.

Test Specimens

Example 1 was prepared by cutting a 120 mm by 40 mm by 18 mm thick layer piece of a foam material, Pure Foam Cushion, Distributed by Michaels Stores Inc. package contained two piece of foam cushion material sized 38.1 cm by 43.1 cm by 2.5 cm, and placing it on a piece of nonwoven, Item F0546 Style S2802KS1BA01A, 28 gsm from Fitesa, folding the nonwoven over the foam and heat sealing the three open edges adjacent the edges of the foam and then trimming any excess nonwoven to create the example blocking member. Two pieces of a 13 mm wide by 120 mm long adhesive coated YHK-5830 HV Series hook material (available from 3M Company in St. Paul, Minn.) were placed on one side of the prototype blocking member approximately at the longitudinal edges of the foam.

Example 2 was prepared as per example 1 except that 12 mm thick foam piece was used.

Example 3 was prepared as per example 1 except a 7 mm thick piece of foam was used.

Example 4 was prepared as per example 1 except a 5 mm thick piece of foam was used.

Example 5 was prepared as per example 1 except 120 mm by 40 mm by 22 mm piece of densified polyester batting (cushion) material, POLY-FIL NU-FOAM, densified polyester, distributed by Michaels Stores Inc. and made by Fairfield, Danbury Conn., was cut from a 38 cm by 43 cm by 5 cm piece of the polyester batting was used in place of the foam of example 1.

Example 6 was prepared as per example 5 except the polyester batting was 19 mm thick.

Example 7 was prepared as per example 5 except the polyester batting was 14 mm thick.

Example 8 was prepared as per example 5 except the polyester batting was 8 mm thick.

Example 9 was prepared as per Example 1 except the foam was 12 mm thick and 20 mm wide by 120 mm long, and only one piece of 13 mm wide PSA coated hook was used.

Diapers 1-9 were prepared by attaching the blocking members of Examples 1-9 to the inside of the diaper approximately centered from side to side and about 8 mm inside the rear waist edge of the diaper, and then placing the diaper on the test apparatus as described above.

Control is a diaper with no blocking member added. All diapers tested were Up and Up Brand size 4 diapers.

Test Results

| Diaper | Result |
| --- | --- |
| 1 | passed (3 passes of 4.5 pound roller) |
| 2 | passed (3 passes of 4.5 pound roller) |
| 3 | failed on first pass of 4.5 pound roller |
| 4 | failed on first pass of 4.5 pound roller |
| 5 | passed (3 passes of 4.5 pound roller) |
| 6 | passed (3 passes of 4.5 pound roller) |
| 7 | passed (3 passes of 4.5 pound roller) |
| 8 | failed on first pass of 4.5 pound roller |
| 9 | passed (3 passes of 4.5 pound roller) |
| Control | failed on first pass of 4.5 pound roller (five individual control diapers tested and all failed on first pass of roller) |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A diaper assembly comprising:
a diaper comprising an inner surface and a rear edge; and a blocking member coupled to a portion of the inner surface, the blocking member having an elongated shape, the direction of elongation oriented along a direction approximately parallel to the rear edge edge to seal against the intergluteal cleft of a wearer and prevent bodily waste from reaching the rear edge of the diaper, the blocking member comprising:
a resilient pad coextensive with the portion of the inner surface; and
an attachment layer bonded to the resilient pad and capable of being repositionably attached to the inner surface at a plurality of locations, wherein the resilient pad comprises a resilient core, and a shell having a top shell layer and a bottom shell layer and surrounding the resilient core, and wherein peripheral edges of the top shell layer are sealed with the peripheral edges of the bottom shell layer along a seam to provide an enclosure that snugly fits the resilient core.

2. The diaper assembly of claim 1, wherein the attachment layer is bonded to the shell.

3. The diaper assembly of claim 2, wherein the shell comprises a nonwoven web.

4. The diaper assembly of claim 1, wherein the attachment layer has an outer surface and a male element of a mechanical fastener disposed on the outer surface.

5. The diaper assembly of claim 4, wherein the male element of the mechanical fastener comprises a replicated hook material that is reticulated.

6. The diaper assembly of claim 4, wherein the diaper comprises a nonwoven top sheet that engages, and mechanically retains, the male element of the mechanical fastener.

7. The diaper assembly of claim 1, wherein the attachment layer comprises a pressure sensitive adhesive.

8. The diaper assembly of claim 1, wherein the attachment layer is discontinuous.

9. The diaper assembly of claim 1, wherein the resilient pad comprises a closed-cell polyethylene foam, an open cell polyurethane foam, or polyester batting.

10. The diaper assembly of claim 9, wherein the foam compresses to at least 50 percent of its uncompressed thickness under a load of 250 grams per square centimeter and recovers to at least 80 percent of its original thickness after being compressed to 50 percent of its original thickness for 10 minutes, wherein recovery occurs within 30 seconds after removal of compressive force.

11. The diaper assembly of claim 1, wherein the resilient pad has a thickness, defined along a direction perpendicular to the inner surface, ranging from 5 millimeters to 20 millimeters.

12. A method of reducing leakage from a diaper, comprising the steps of:
providing an elongated blocking member having a resilient pad and an attachment layer bonded to the resilient pad, the attachment layer being attachable to an inner surface of the diaper wherein the elongated blocking member has an elongated shape, the direction of elongation oriented along a direction approximately parallel to a rear edge of the diaper;
coupling the attachment layer to a portion of the inner surface to provide a diaper assembly, wherein the blocking member is coextensive with the portion of the inner surface; and
fastening the diaper assembly to a wearer whereby the blocking member conforms to contours of the wearer's intergluteal cleft and prevents any discharged bodily waste from leaking out of the diaper,
wherein the resilient pad comprises a resilient core, and a shell having a top shell layer and a bottom shell layer and surrounding the resilient core, and wherein peripheral edges of the top shell layer are sealed with the peripheral edges of the bottom shell layer along a seam to provide an enclosure that snugly fits the resilient core.

13. The method of claim 12, wherein the attachment layer is releasably attachable to the inner surface of the diaper.

14. The method of claim 12, wherein the attachment layer is repositionable such that the blocking member can be subsequently detached from the inner surface and reattached to a different portion of the inner surface of the same or a different diaper.

* * * * *

UNITED STATES PATENT AND TRADEMARK OFFICE
CERTIFICATE OF CORRECTION

PATENT NO. : 10,925,777 B2
APPLICATION NO. : 15/535084
DATED : February 23, 2021
INVENTOR(S) : Leigh Wood It is certified that error appears in the above-identified patent and that said Letters Patent is hereby corrected as shown below:

In the Specification

Column 2
Lines 27-28, delete "FIG. 1 is a plan view of an exemplary finished diaper assembly." and insert the same on Column 2, Line 28, as a new paragraph.

In the Claims

Column 13
Line 4, in Claim 1, delete "edge edge" and insert -- edge --, therefor.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*